US012684301B2

(12) United States Patent
Mitra et al.

(10) Patent No.: US 12,684,301 B2
(45) Date of Patent: Jul. 14, 2026

(54) OPERATION OF A HEARING DEVICE IN AN AUDIO PRESENTATION SYSTEM

(71) Applicant: Sivantos Pte. Ltd., Singapore (SG)

(72) Inventors: Subhasri Mitra, Erlangen (DE); Andreas Pfrommer, Erlangen (DE)

(73) Assignee: Sivantos Pte. Ltd., Singapore (SG)

( * ) Notice: Subject to any disclaimer, the term of this patent is extended or adjusted under 35 U.S.C. 154(b) by 136 days.

(21) Appl. No.: 18/675,953

(22) Filed: May 28, 2024

(65) Prior Publication Data

US 2024/0397271 A1    Nov. 28, 2024

(30) Foreign Application Priority Data

May 26, 2023    (DE) ..................... 10 2023 204 982.1

(51) Int. Cl.
H04R 25/00        (2006.01)
A61B 5/00        (2006.01)
(Continued)

(52) U.S. Cl.
CPC .......... H04R 25/554 (2013.01); A61B 5/1117 (2013.01); A61B 5/7465 (2013.01);
(Continued)

(58) Field of Classification Search
CPC .... H04R 25/50; H04R 25/505; H04R 25/554; H04R 2225/41; H04R 2225/51; H04R 2225/55; A61B 5/1117; G06F 3/0346
See application file for complete search history.

(56) References Cited

U.S. PATENT DOCUMENTS 4,824,375  A  *  4/1989  Weiner ................... G09B 5/062
                                                    434/319
5,461,371  A  *  10/1995  Matsumoto ............. G09F 27/00
                                                    340/8.1
(Continued)

FOREIGN PATENT DOCUMENTS

EP        2835782 A1    2/2015
EP        3709677 A1    9/2020

OTHER PUBLICATIONS

English Language Translation of EP3709677A1, pp. 1-9, Sep. 16, 2020. (Year: 2020).*
(Continued)

*Primary Examiner* — Paul W Huber
(74) *Attorney, Agent, or Firm* — Laurence A. Greenberg; Werner H. Stemer; Ralph E. Locher

(57)        ABSTRACT
A method operates a hearing device in an audio presentation system. In this case, the hearing device has a wideband transmitter and a narrowband receiver. The audio presentation system has a plurality of audio transmitters that operate using narrowband transmission and are arranged so as to be spatially at a distance from one another in the intended usage state, and a plurality of wideband transmitters that are arranged so as to be spatially at a distance from one another in the intended usage state. A variable that is characteristic of a position of a hearing device relative to the audio transmitters is initially ascertained by the wideband transmitters of the hearing device and of the audio presentation system. A specific one of the multiple audio transmitters of the audio presentation system is then selected to transmit audio to the hearing device on the basis of this characteristic variable.

13 Claims, 1 Drawing Sheet

(51) Int. Cl.
  *A61B 5/11* (2006.01)
  *G06F 3/0346* (2013.01)

(52) U.S. Cl.
  CPC ......... *G06F 3/0346* (2013.01); *H04R 25/505*
    (2013.01); *H04R 2225/51* (2013.01)

(56) References Cited

U.S. PATENT DOCUMENTS

| | | | | |
|---|---|---|---|---|
| 5,796,351 A * | 8/1998 | Yabuki | ................. | G06Q 20/202 |
| | | | | 340/10.5 |
| 5,797,125 A * | 8/1998 | Hirohama | ................ | G09B 5/04 |
| | | | | 704/277 |
| 5,929,848 A * | 7/1999 | Albukerk | .............. | G09B 5/065 |
| | | | | 340/4.62 |
| 6,985,240 B2 * | 1/2006 | Benke | ..................... | G06F 16/29 |
| | | | | 356/614 |
| 7,308,486 B2 * | 12/2007 | Althin | ..................... | H04L 67/51 |
| | | | | 709/219 |
| 8,090,459 B2 * | 1/2012 | Hsu | ...................... | H04B 10/116 |
| | | | | 381/77 |
| 9,143,881 B2 * | 9/2015 | Fan | .................... | G06Q 20/3224 |
| 9,264,854 B2 * | 2/2016 | Kokubo | .................. | H04W 4/02 |
| 9,324,202 B2 | 4/2016 | Lindig et al. | | |
| 9,600,720 B1 * | 3/2017 | Gray | ...................... | G06F 18/25 |
| 9,866,916 B1 * | 1/2018 | Boss | ................ | H04N 21/41415 |
| 10,959,051 B2 * | 3/2021 | Dunn, Jr. | .............. | H04W 4/024 |
| 11,343,633 B2 * | 5/2022 | Tomlin | .................... | H04S 7/303 |
| 2006/0168300 A1 * | 7/2006 | An | .......................... | G09B 5/125 |
| | | | | 709/228 |
| 2007/0274685 A1 * | 11/2007 | Hale | ..................... | G06F 16/487 |
| | | | | 386/218 |
| 2020/0007988 A1 * | 1/2020 | Raj | ........................ | H04W 4/023 |
| 2023/0073936 A1 | 3/2023 | Pedersen et al. | | |
| 2023/0412993 A1 * | 12/2023 | Kalbermatter | ..... | G06K 7/10306 |
| 2024/0273990 A1 * | 8/2024 | Pham | .................... | A61B 5/7246 |
| 2024/0276170 A1 * | 8/2024 | Tomlin | .................... | G06F 3/165 |

OTHER PUBLICATIONS

Yang et al., Ear-AR: Indoor Acoustic Augmented Reality on Earphones, MobiCom '20: Proceedings of the 26th Annual International Conference on Mobile Computing and Networking, Sep. 21-25, 2020, London, UK., pp. 745-758, ISBN 978-1-4503-7085-1, https://doi.org/10.1145/3372224.3419213.

Hashem et al., Leveraging Earables for Natural Calibration-Free Multi-Device Identification in Smart Environments, HotMobile 2021: Proceedings of the 22nd International Workshop on Mobile Computing Systems and Applications, Feb. 2021, virtual, pp. 92-98, ISBN 978-1-4503-8323-3, https://doi.org/10.1145/3446382.3448653.

* cited by examiner

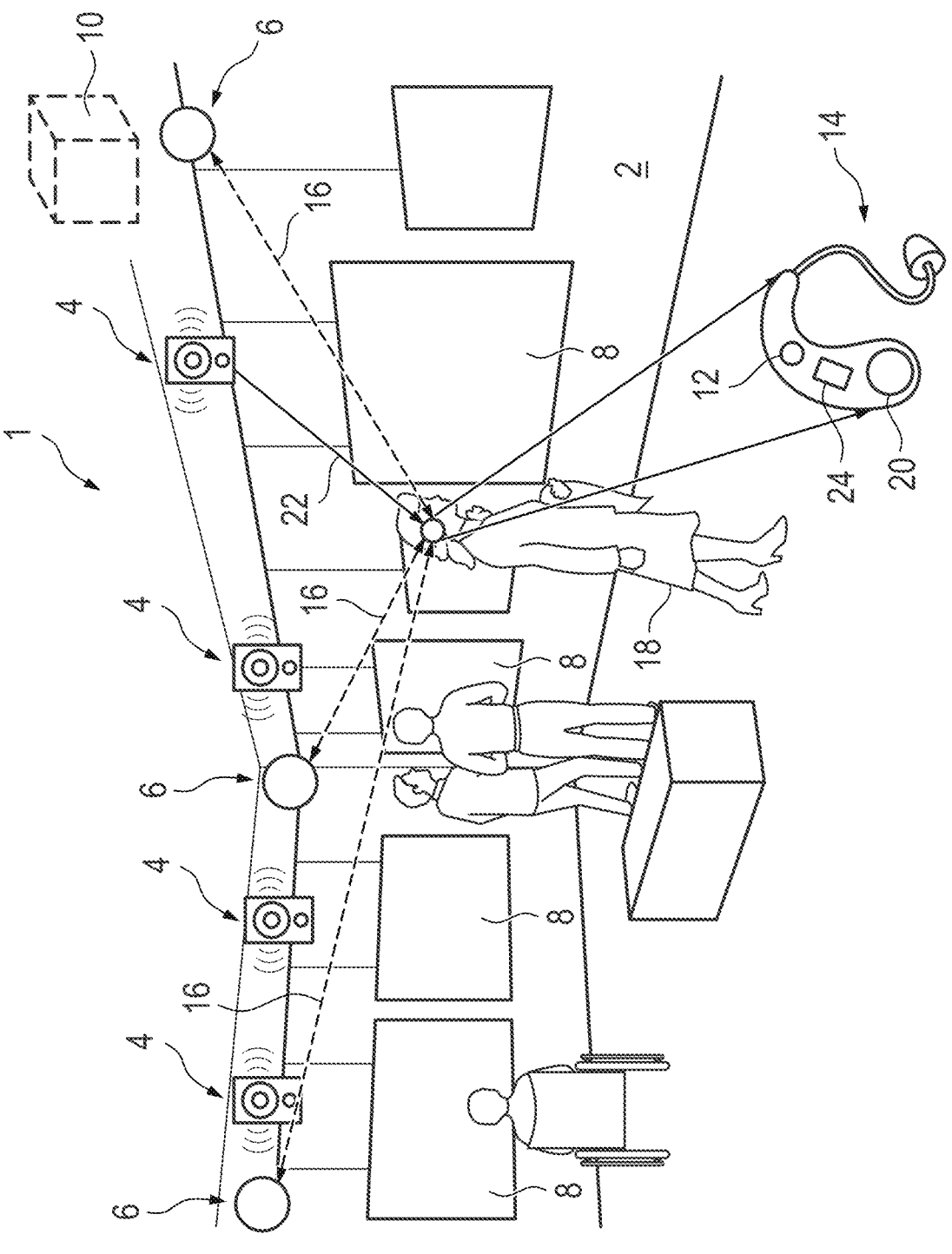

OPERATION OF A HEARING DEVICE IN AN AUDIO PRESENTATION SYSTEM

FIELD AND BACKGROUND OF THE INVENTION

The invention relates to a method for operating a hearing device in an audio presentation system. In addition, the invention relates to such an audio presentation system. Furthermore, the invention also relates to a hearing device.

Hearing devices are typically used to output an audio signal to the hearing of the wearer of this hearing device. The output takes place by means of an output transducer, usually acoustically via airborne sound by means of a loudspeaker (also referred to as a "receiver"). Such hearing devices are frequently used as what are known as hearing aid equipment (also, for short: hearing aids). In this regard, the hearing devices normally comprise an acoustic input transducer (in particular a microphone) and a signal processor (also: controller) that is configured to process the input signal (also: microphone signal) generated by the input transducer from the ambient sound with application of at least one typically user-specific stored signal processing algorithm in such a way that a hearing loss of the wearer of the hearing device is at least partially compensated for. In particular in the case of hearing aid equipment, the output transducer may be, in addition to a loudspeaker, alternatively also what is known as a bone vibrator or a cochlear implant, which are configured for mechanical or electrical coupling of the sound signal into the hearing of the wearer. The term hearing devices also additionally includes in particular equipment such as, e.g., what are known as tinnitus maskers, headsets, headphones, and the like.

Typical designs of hearing devices, in particular hearing aids, are behind-the-ear (BTE) and in-the-ear (ITE) hearing devices. These designations are indicative of the intended wearing position. Therefore, behind-the-ear hearing devices have a (main) housing that is worn behind the pinna. In this context, a distinction may be made between models whose loudspeaker is arranged in this housing—in this case, the sound is typically output to the ear by means of a sound tube worn in the auditory canal—and models having an external loudspeaker that is placed in the auditory canal. In-the-ear hearing devices, on the other hand, have a housing that is worn in the pinna or even entirely in the auditory canal.

Hearing devices, in particular hearing aids, are often configured to receive audio signals non-acoustically, for example by means of what are known as telephone coils. These are configured to receive signals transmitted by inductive coupling in order to then output said signals via the loudspeakers. In addition to telephony, this is in particular also used to provide audio information in public spaces and to then process said information in a hearing device. This may also involve, inter alia, audio transmission in the event of a lecture, which, in addition to conventional output via loudspeakers, may also be carried out in part by means of corresponding coils for hearing-aid wearers, and so a hearing aid is able to pick up said audio transmission and correspondingly output same to the wearer, in particular with reduced interference due to background noise. By way of example, this is also used, however, to provide what are known as audio guides for hearing-aid wearers in a museum. The disadvantage of this is that an inductive, i.e. electromagnetic, transmission over relatively large distances, for example in lecture halls or museum spaces, may be comparatively ineffective and affected by interference.

SUMMARY OF THE INVENTION

The invention is based on the object of improving provision of audio information to a hearing-aid wearer.

This object is achieved according to the invention by a method having the features of the independent method claim. In addition, this object is achieved according to the invention by an audio presentation system having the features of the independent audio presentation system claim. Furthermore, this object is achieved according to the invention by a hearing device having the features of the independent hearing device claim. Advantageous embodiments and refinements of the invention, which are partially inventive as such, are represented in the dependent claims and the following description.

The method according to the invention is used for operating a hearing device in an audio presentation system. In this case, the hearing device has a wideband transmitter and a narrowband receiver. The audio presentation system has a plurality of audio transmitters that operate using narrowband transmission and are arranged so as to be spatially at a distance from one another in the intended usage state, and a plurality of wideband transmitters that are arranged so as to be spatially at a distance from one another in the intended usage state. In the course of the method according to the invention, a variable that is characteristic of a position of a hearing device relative to the audio transmitters is initially ascertained by means of the wideband transmitters of the hearing device and of the audio presentation system. A specific one of the multiple audio transmitters of the audio presentation system is then selected to transmit audio to the hearing device on the basis of this characteristic variable.

The audio presentation system according to the invention is configured and provided to be used in the course of the method described here and in the following. In particular, the audio presentation system therefore has the physical features that are described in the course of the method for the audio presentation system, but optionally also, at the same time, the corresponding method features (and therefore also the resulting advantages) (and also accordingly conversely, the method described here and in the following has the features of the audio presentation system and the advantageous configurations thereof). The audio presentation system therefore has the plurality of audio transmitters (optionally also referred to as "audio broadcasting transmitters") that operate using (preferably digital) narrowband transmission and are arranged so as to be spatially at a distance from one another in the intended usage state. These audio transmitters are preferably configured to transmit (also: to "stream" or to transmit as a "cast") together an item of audio information, or in each case individually a separate item of audio information, to a radio receiver (for example a remote station coupled using radio transmission technology), in particular a narrowband receiver (optionally a narrowband transmitter). The audio presentation system additionally has the plurality of wideband transmitters that are arranged so as to be spatially at a distance from one another in the intended usage state. The audio presentation system also has a controller that is connected to the audio transmitters and the wideband transmitters using data transmission technology.

This controller is optionally configured to ascertain the variable, which is described above and is characteristic of the position of the hearing device relative to the audio transmitters, by means of the wideband transmitters. The controller is further optionally additionally configured to select at least one audio transmitter to transmit audio (in particular what is known as a broadcast) to the hearing device on the basis of this characteristic variable.

The audio presentation system is therefore preferably configured "to broadcast" audio information by means of at least one of multiple spatially distributed audio transmitters, such that a remote station (that is optionally coupled explicitly, i.e. by means of a type of "handshake"), in particular the hearing device, is able to receive this broadcast audio information and in particular is able to output it to a person using the hearing device ("hearing-aid wearer").

According to the method, an item of position information for the hearing device relative to the audio transmitters is ascertained by means of the wideband transmitters and, depending on this information, a selection is made as to from which audio transmitter the hearing device is intended to receive the (correspondingly assigned) audio transmission.

On account of the position-dependent selection, according to the invention, of the audio transmitter, and therefore possibly also the specific audio information thereof, a comparatively effective transmission may be enabled, since the audio information does not need to be broadcast over a large spatial area, but rather may be output in an approximately individualized manner.

In one preferred method variant, the narrowband receiver of the hearing device (in particular according to, or depending on, the selection described above) is actuated to connect to a broadcast audio transmission of the specific audio transmitter. For this purpose, an item of information is also expediently provided to the hearing device (for example by means of the wideband transmitters of the audio presentation system), on the basis of which information the selected audio transmitter is able to be detected. As part of this information, for example, an identifier for that audio transmitter to which the hearing device is intended to be coupled for audio transmission, or to the audio transmission of which the hearing device, specifically the narrowband transmitters thereof, is intended to connect, is transmitted to the hearing device, for example. This identifier is expediently concomitantly output by the respective audio transmitter in its audio transmission, for example as a type of meta information.

In one preferred method variant, a distance between the hearing device and the audio transmitters, in particular each of the audio transmitters, is ascertained as the characteristic variable. That audio transmitter that is closest to the hearing device is then selected to transmit audio to the hearing device. As a result, it is possible to keep transmission powers on the part of the audio transmitters as low as possible, since it may be possible to reduce transmission ranges in comparison with a transmission to an unknown position of a receiver. It is optionally therefore also possible for only specific audio transmitters, in the range or "transmission range" of which there is currently a hearing device (or at least a narrowband receiver of comparable equipment), to be active. The latter also contributes to a reduced power consumption. In particular, such a procedure may be advantageous, for example, in a museum, however. In this case, the audio presentation system may constitute an output interface for what is known as an audio guide, by means of which information relating to individual exhibits may be output to corresponding receivers. In this case, the hearing device may be personal equipment of a person, for example their hearing aid, but in principle it may also be a headset provided by the museum. In this case, an audio transmitter may, for example, be associated with exactly one exhibit and output one item of information relating to this exhibit. On the basis of the procedure described above and in the following, it is therefore advantageously possible to detect the exhibit in front of which the person is currently located, and to select the audio transmission of the corresponding audio transmitter. It is therefore possible to dispense with a manual selection of an audio transmission for this exhibition item. It is likewise possible, however, to also output specific information in public areas, for example an airport or train station, to a passenger by means of the closest audio transmitter, for example timetable information, information relating to a boarding time at a specific gate, or the like. For this procedure, the distance between the wideband transmitters of the audio presentation system and the audio transmitters thereof is expediently known.

Optionally, the position of the hearing device in the space (for example in an exhibition space of the museum) is also deduced by individual distance values between the hearing device and at least two, but preferably more than two, wideband transmitters of the audio presentation system being deduced. On the basis of these multiple distance values, the position of the hearing device may be determined as the point of intersection of the circles, which are described by each distance value, around the respective wideband transmitter of the audio presentation system. Three distance values are often sufficient to clearly determine the position. In this case, the respective position of the audio transmitters in the corresponding space is also known, and so the arrangement of the audio transmitters relative to the hearing device is able to be ascertained by a position comparison.

The audio transmitters are preferably configured to transmit audio according to the Auracast (in particular referred to by the trademark "Auracast Broadcast Audio") audio transmission technology. This is based in particular on the Bluetooth Low Energy radio standard, which uses a narrowband transmission in the 2.4 GHz band, in particular divided into 40 channels with a width of 2 MHz. In this case, Auracast is specifically a broadcasting protocol, which therefore in particular provides an information signal to a multiplicity of potentially unknown receivers.

Further preferably, a receiver that operates according to the Bluetooth radio standard, in particular a transceiver (that is therefore additionally configured for transmission purposes, and is also referred to as a transmitter or as a Bluetooth module), is accordingly used as the narrowband receiver of the hearing device.

In one preferred embodiment, the wideband transmitters are in the form of ultra-wideband transmitters (for short: UWB transmitters) (i.e. such UWB transmitters are used in a corresponding method variant). These operate with a frequency width of at least 500 MHz and/or of at least 20% of a mid-frequency. In this context, the mid-frequency should be understood to mean, in particular, the mean value of the upper and lower limit frequency of the corresponding frequency band. By contrast, conventional radio technology provided for such uses (narrowband radio or narrowband communication) uses significantly narrower frequency widths, in particular frequency widths measured as less than half of this (for example, WLAN with at most approximately 160 MHz in the 5 GHz band, otherwise less than 100 MHz; Bluetooth likewise below 100 MHz). In addition, the UWB transmitter is preferably configured to transmit only individual signal pulses (preferably in the range of less than 10 ns, in part of the order of 1 ns). In contrast to conventional radio technology (in particular WLAN and Bluetooth), there is no modulation of the carrier signal, specifically its carrier frequency, here; instead, use is made of pulse modulation techniques in particular.

In one advantageous method variant, the characteristic variable is ascertained on the basis of a signal propagation time measurement and/or determination of an angle of arrival (for example, of a signal transmitted by the wideband transmitter of the hearing device, or vice versa). This has the advantage that it is possible to achieve a comparatively high spatial resolution, i.e. high precision of the position or even of the distance between the hearing device and the respective audio transmitter, as a result. The angle of arrival is ascertained in particular by means of two (reception) antennas associated with the respective wideband transmitter.

Preferably, the wideband transmitters of the audio presentation system are used as what are known as anchor points. These are configured to receive a ping signal from the wideband transmitter of the hearing device, which signal is then used in turn to ascertain the position of the hearing device or the characteristic variable.

The wideband transmitters of the audio presentation system, in particular respectively associated internal clocks, are expediently synchronized with one another (optionally via an actuation by way of the controller of said audio presentation system). As a result, it is possible to carry out the signal propagation time measurement described above in a particularly precise manner, since signal propagation time differences between the individual wideband transmitters are thus able to be detected more accurately. The wideband transmitters are optionally connected by means of a data cable for this purpose. This synchronization may optionally also be carried out on a radio basis, however. An internal clock of the controller may optionally be used as a reference, in particular the controller may thus trigger the wideband transmitters to synchronize to the internal clock thereof.

In a further expedient method variant, signals to be received by the wideband transmitters of the audio presentation system (for example, the ping signals mentioned above) are transmitted by the wideband transmitter of the hearing device. A movement of the person wearing the hearing device is then deduced on the basis of these signals being received by the wideband transmitters (anchor points). In this case, this movement is in particular deduced from a temporal profile of the above-described distance values or angles of arrival. Assuming that the person is wearing the hearing device on their head and the wideband transmitter of the hearing device is likewise arranged on their head, it is also possible to deduce, on account of the precise spatial resolution when determining the variable that is characteristic of the position of the hearing device, a head movement (in particular on the basis of the temporal profile of the variable or position of the hearing device) and/or an orientation of the head of the person. A viewing direction, and therefore a spatial interest, of the person may in turn be deduced from this information. In one optional configuration of the invention, the content of the audio transmission is adapted to this information (i.e. changed) in order to therefore improve a spatial perception. By way of example, this may be used in a cinema or even in the case of a TV set in order, when the person looks to the side, to perceive noises that are intended to be perceived as coming from the scene on the screen in that way, and to not always obtain the same acoustic impression when the head is turned. For this purpose, the balance of a stereo or surround signal may in particular be changed depending on the viewing direction.

Alternatively or additionally to the above-described adjustment of the content of the audio transmission, monitoring of the person wearing the hearing device is enabled and is also carried out. A fall by the person is deduced on the basis of the above-described ascertained movement of the hearing device, for example if a range of movement in the vertical direction corresponds to the height of the person or at least exceeds a predefined extent (for example more than 1.2 or 1.4 meters), and it is therefore comparatively unlikely that the person has sat down. If a fall by the person is deduced by the controller in this way, optionally an emergency call is made and/or a query is output by the hearing device. Both the emergency call and the query may be made/output by the hearing device itself. Alternatively, this may also in principle be carried out by the audio presentation system, however.

In one expedient configuration, (in particular exactly) one wideband transmitter (anchor point) is associated with each audio transmitter. The respectively associated wideband transmitter is preferably also spatially associated with the audio transmitter. In this case, the respective wideband transmitter is expediently arranged so as to be closer to the corresponding audio transmitter than to the closest one of the other audio transmitters. This makes it possible to associate the closest audio transmitter with the hearing device in a particularly simple manner.

The anchor points mentioned above may optionally also be provided independently of the audio presentation system, however, for example they may also be incorporated into a home surveillance system.

According to one optional configuration, the method described above is at least predominantly carried out by the controller of the audio presentation system. In this case, the "selection" made of the audio transmitter is conveyed to the hearing device, wherein the hearing device "only" implements this selection by connecting to the corresponding audio transmission (i.e. in particular, the narrowband receiver is actuated to receive the audio transmission of the selected audio transmitter, preferably on the basis of the identifier mentioned above). In particular, the characteristic variable is therefore ascertained by the audio presentation system on the basis of a signal being received by the wideband transmitter of the hearing device. Alternatively, the method described above is at least predominantly carried out by the hearing device, for example by means of a signal processor, but preferably on associated equipment (that is coupled to the hearing device using data transmission technology), for example a smartphone. In this case, for example, the characteristic variable may likewise be ascertained by the audio presentation system and be transmitted to the hearing device for further evaluation, or the wideband transmitters of the audio presentation system transmit, as a response to the (ping) signal from the wideband transmitters of the hearing device, a separate signal that, for example, contains the—preferably synchronized—transmit time and preferably also the identifier of the associated audio transmitter, and therefore the characteristic variable is able to be determined, and the corresponding audio transmitter is able to be selected as a result, by the hearing device (for example in the smartphone) on the basis of this response.

As described above, the hearing device according to the invention has the narrowband receiver (for example the Bluetooth module) that is configured to receive audio signals (i.e. from the audio transmission) (in particular output by the audio transmitter), the wideband transmitter and a signal processor. In this case, the latter is coupled to the narrowband receiver and the wideband transmitter using data transmission technology. In addition, the hearing device is configured to be used with the audio presentation system described above, preferably by means of corresponding programming of the signal processor.

The wideband transmitter of the hearing device is expediently configured to communicate with the narrowband transmitters of the audio presentation system, in particular therefore to transmit and receive in the same frequency band (and in particular also to use the same radio standard).

In one optional configuration, the signal processor of the hearing device is configured to carry out the above-described method independently. To this end, information that may be required, in particular the above-described identifiers of the audio transmitters, optionally the signal propagation times ascertained, for example, by the controller of the audio presentation system, angles of arrival and/or also the distance values or position of the hearing device relative to the audio transmitters, is conveyed to the signal processor, in particular by means of the wideband transmitters. The hearing device is, however, preferably coupled to a smartphone or other equipment using data transmission technology during operation as intended, which smartphone or equipment has remote control software installed thereon for the hearing device, wherein the abovementioned information is provided to this remote control software. In this case, this remote control software is configured to carry out the above-described method, in particular to select the corresponding audio transmitter and to transmit this information to the hearing device. This remote control software (in particular a (micro)processor executing this software) therefore ascertains the characteristic variable on the basis of the signal exchange between the wideband transmitters of the hearing device and of the audio presentation system, and in turn selects the corresponding audio transmitter on the basis thereof.

In this case, characteristic means in particular that the characteristic variable contains quantitative information relating to the position of the hearing device relative to the wideband transmitters, and it is therefore possible to infer the position, but at least clearly the distance, from the characteristic variable. In this case, the characteristic variable may directly indicate the variable (for example the value) of the respective position (in particular of the distance). The characteristic variable may, however, also be a variable that is directly or indirectly proportional to the position or the distance to be displayed, or has a non-linear, for example a logarithmic, exponential or polynomial (i.e. quadratic, cubic, etc.), relationship with said position or distance.

In the context of the invention, the controller of the audio presentation system and the signal processor may be in the form of a non-programmable electronic circuit. However, in the context of the invention, the controller or signal processor may also be formed by a microcontroller, in which the above-described functionality is implemented in the form of a software module. The processor of the smartphone or of the external equipment is preferably in the form of a microcontroller.

The conjunction "and/or" here and in the following is to be understood, in particular, to mean that features linked by means of this conjunction can be implemented both jointly and as alternatives to each other.

BRIEF DESCRIPTION OF THE FIGURES

One exemplary embodiment of the invention is explained in more detail below with reference to a drawing, in which the single FIGURE, FIG. 1, schematically shows an audio presentation system in an intended usage state.

DETAILED DESCRIPTION OF THE INVENTION

FIG. 1 shows an audio presentation system 1 that is installed in an exhibition space 2. The audio presentation system 1 has multiple, in this case specifically four, audio transmitters 4 that are configured to operate according to the Bluetooth Low Energy radio standard, specifically for "Auracast Broadcast Audio" (registered trademark). Furthermore, the audio presentation system 1 has multiple, in this case specifically three, wideband transmitters, which are subsequently referred to as UWB anchors 6. The audio transmitters 4 and the UWB anchors 6 are distributed at a distance from one another in the exhibition space 2. The audio transmitters 4 are spatially associated with a respective displayed image 8. The audio transmitters 4 are configured to broadcast an audio transmission, the content of which relates to the respective image 8. An audio guide for the exhibition space 2 may thus be produced. The audio transmitters 4 and the UWB anchors 6 are connected (in a wired manner or by radio) to a controller 10 in order to exchange data.

The UWB anchors 6 are specifically used to pick up, i.e. to receive, a ping signal from a wideband transmitter—subsequently referred to as UWB transmitter 12 for short—of a hearing device 14, and subsequently to enter into a signal exchange therewith (see bidirectional, dashed arrows 16). In the present example, a person 18 is wearing this hearing device 14. A distance between the hearing device 14, that is to say the person 18, and the respective UWB anchors 6 is ascertained on the basis of this signal exchange with multiple of the UWB anchors 6. This ascertainment may, for example, be carried out by the controller 10 of the audio presentation system 1. To this end, the controller 10 ascertains the signal propagation time between each UWB anchor 6 and the UWB transmitter 12 as a characteristic variable for the relative position of the hearing device 14 in relation to the UWB anchors 6, and therefore, assuming knowledge of the arrangement of the audio transmitters 4 in relation to the UWB anchors 6, also in relation to the audio transmitters 4. In this case, the position of the hearing device 14 in the exhibition space 2 is ascertained, for example, as the point of intersection of circles, with the corresponding distance values as the radius, around the corresponding UWB anchor 6.

If the controller 10 has ascertained the position of the hearing device 14, at least which audio transmitter 4 is the closest one to the hearing device 14, and therefore to the person 18, the controller 10 outputs this information, together with an identifier for the corresponding audio transmitter 4, to the hearing device 14. The hearing device 14 then has a narrowband receiver 20 for receiving the audio signals sent by means of this audio transmitter 4 (solid, unidirectional arrow 22).

The hearing device 14 also has a signal processor 24. Said signal processor is configured to accordingly actuate the UWB transmitter 12 or the narrowband receiver 20 to communicate with the UWB anchors 6 and the corresponding audio transmitter 4.

Alternatively, the above-described ascertainment of the closest audio transmitter 4 is carried out on the basis of the signal exchange, but also by way of the signal processor 24 or a smartphone (not shown) that is coupled to the hearing device 14 using data transmission technology. In this case, the signal processor (or the smartphone to which the hearing device 14 transmits the corresponding data) evaluates the signals received from the UWB anchors 6 and thereby ascertains the respective distance thereto. In this case, an identifier for the respective audio transmitter 4 is transmitted by the UWB anchor 6, and so the signal processor 24 (or the smartphone) is able to select the closest audio transmitter 4 itself and also connect to its audio transmission.

The subject matter of the invention is not restricted to the above-described exemplary embodiment. Rather, further embodiments of the invention can be derived by a person skilled in the art from the above description.

LIST OF REFERENCE SIGNS

1 Audio presentation system
2 Exhibition space
4 Audio transmitter
6 UWB anchor
8 Image
10 Controller
12 UWB transmitter
14 Hearing device
16 Arrow
18 Person
20 Narrowband receiver
22 Arrow
24 Signal processor

The invention claimed is:

1. A method for operating a hearing device, having a wideband transmitter and a narrowband receiver, in an audio presentation system having a plurality of audio transmitters that operate using narrowband transmission and are disposed so as to be spatially at a distance from one another in an intended usage state, and a plurality of wideband transmitters that are disposed so as to be spatially at a distance from one another in the intended usage state, which comprises the method steps of:

ascertaining a characteristic variable being characteristic of a position of the hearing device relative to the audio transmitters by means of the wideband transmitters of the hearing device and of the audio presentation system;

selecting a specific one of the plurality of audio transmitters of the audio presentation system to transmit audio to the hearing device on a basis of the characteristic variable;

transmitting signals to be received by the wideband transmitters of the audio presentation system by the wideband transmitter of the hearing device, and wherein a movement of a person wearing the hearing device is deduced on a basis of the signals being received; and deducing a head movement and/or an orientation of a head of the person wearing the hearing device on a basis of the signals from the wideband transmitter of the hearing device received by means of the wideband transmitters of the audio presentation system, and content of an audio transmission is changed depending on the head movement or the orientation of the head.

2. The method according to claim 1, wherein the narrowband receiver of the hearing device is actuated to connect to a broadcast audio transmission of the specific one of the plurality of audio transmitters.

3. The method according to claim 1, which further comprises ascertaining a distance between the hearing device and the audio transmitters as the characteristic variable and the audio transmitter closest to the hearing device is selected to transmit audio to the hearing device.

4. The method according to claim 1, which further comprises using a transceiver operating according to a Bluetooth radio standard as the narrowband receiver of the hearing device.

5. The method according to claim 1, which further comprises using an ultra-wideband transmitter as a respective one of the wideband transmitters.

6. The method according to claim 1, which further comprises ascertaining the characteristic variable on a basis of a signal propagation time measurement and/or determination of an angle of arrival.

7. The method according to claim 1, which further comprises using the wideband transmitters of the audio presentation system as anchor points, wherein a ping signal from the wideband transmitter of the hearing device is received by means of the anchor points and is used to determine the position of the hearing device.

8. The method according to claim 1, which further comprises synchronizing associated internal clocks of the wideband transmitters of the audio presentation system with one another.

9. The method according to claim 1, which further comprises deducing a fall by the person on a basis of an ascertained movement of the person and an emergency call is made and/or a query is output by the hearing device if the fall is detected.

10. An audio presentation system, comprising:

a plurality of audio transmitters operating using narrowband transmission and are disposed so as to be spatially at a distance from one another in an intended usage state;

a plurality of wideband transmitters disposed so as to be spatially at a distance from one another in the intended usage state; and a controller connected to said audio transmitters and said wideband transmitters using data transmission technology, wherein the audio presentation system configured for performing the method according to claim 1.

11. The audio presentation system according to claim 10, wherein each of said wideband transmitters is associated with one of said audio transmitters.

12. The audio presentation system according to claim 10, wherein a respective one of said wideband transmitters is disposed so as to be closer to a corresponding one of said audio transmitters than to a closest one of another one of said audio transmitters.

13. A hearing device, comprising:

a narrowband receiver configured to receive audio signals;

a wideband transmitter; and a signal processor coupled to said narrowband receiver and said wideband transmitter using data transmission technology, wherein the hearing device is configured to perform the method according to claim 1.

* * * * *